(12) United States Patent
Arnold et al.

(10) Patent No.: US 10,548,492 B2
(45) Date of Patent: Feb. 4, 2020

(54) PRESSURE SENSOR

(71) Applicant: MEAS Switzerland S.à.r.l., Bevaix (CH)

(72) Inventors: Thomas Arnold, Monlalchez (CH); Philippe Goguillot, Corcelles (CH); Predrag Drljaca, Neuchatel (CH)

(73) Assignee: MEAS SWITZERLAND S.A.R.L., Bevaix (CH)

( * ) Notice: Subject to any disclaimer, the term of this patent is extended or adjusted under 35 U.S.C. 154(b) by 87 days.

(21) Appl. No.: 15/373,294

(22) Filed: Dec. 8, 2016

(65) Prior Publication Data

US 2018/0160922 A1 Jun. 14, 2018

(51) Int. Cl.
*A61B 5/024* (2006.01)
*A61B 5/00* (2006.01)

(52) U.S. Cl.
CPC ........ *A61B 5/02444* (2013.01); *A61B 5/6801* (2013.01); *A61B 5/7278* (2013.01); *A61B 5/74* (2013.01); *A61B 2562/0247* (2013.01)

(58) Field of Classification Search
CPC ........ A61B 5/02444; A61B 2562/0247; G01L 9/0042
See application file for complete search history.

(56) References Cited

U.S. PATENT DOCUMENTS

| 5,215,096 A * | 6/1993 | Zapf ................. A61B 5/02225 600/493 |
| 6,704,185 B2 * | 3/2004 | Chatzandroulis ....... G01L 1/148 361/283.1 |
| 2012/0247227 A1 | 10/2012 | Crivelli |
| 2015/0266720 A1 | 9/2015 | Furuhata |

FOREIGN PATENT DOCUMENTS

| EP | 1481638 A1 | 12/2014 |
| EP | 2873960 A1 | 5/2015 |
| JP | 2006242757 A | 9/2006 |
| WO | 2012116995 A1 | 9/2012 |

OTHER PUBLICATIONS

International Preliminary Report on Patentability issued in related PCT Application No. PCT/EP2017/081529; dated Jun. 11, 2019.
International Search Report issued in related PCT Application No. PCT/EP2017/081529; dated Feb. 26, 2018.

* cited by examiner

*Primary Examiner* — Alyssa M Alter
(74) *Attorney, Agent, or Firm* — Howard IP Law Group

(57) ABSTRACT

A pressure sensor including a substrate having a first housing defining a gas-filled interior cavity arranged thereon. An elastic sealing element is attached to a free end of the first housing and generally covers an open end of the interior cavity for sealing the interior cavity with respect to an external environment. A portion of the elastic sealing element is configured to be moveable in response to a pressure acting thereon. A semiconductor die is arranged on the substrate and defines a pressure sensing diaphragm exposed to the gas occupying the interior cavity.

14 Claims, 6 Drawing Sheets

PRESSURE SENSOR

FIELD OF THE INVENTION

The application relates to sensors. More particularly, the application relates to sensors for detecting pressures of fluids, including gasses.

BACKGROUND OF THE INVENTION

A pressure sensor (or transducer) converts a pressure acting thereon to an electrical signal as a function of the pressure imposed. These sensors are generally embodied in pressure sensor packages, and include a pressure-sensing device such as a silicon die. Such devices are typically manufactured using micro-machined or Micro-Electro-Mechanical System (MEMS) based techniques. One common technique for manufacturing a pressure sensor package is to attach a MEMS device onto a substrate, such as a ceramic or printed circuit board (PCB) substrate. Enabling circuit components such as application-specific integrated circuits (ASICs), as well as conductive bonding pads and/or electrical traces, may be mounted to or formed on the substrate for electrically connecting to the MEMS device to perform desired functions (e.g. analog to digital conversion and/or amplification).

Various pressure sensor topologies have been developed for a wide variety of applications. One important field of use includes medical applications for monitoring, for example, the heart rate of a patient. Existing sensors used in this field, including wearable devices, utilize a gel-filled housing for transmitting pressure waves from a sensing end thereof that is arranged in contact with a patient, to a pressure-sensitive die also arranged within the gel-filled housing. In addition to providing a pressure-transmitting medium, the gel acts to protect electronic components of the sensor package from moisture and other detrimental environmental characteristics, for example. These gel-filled sensors, however, suffer several drawbacks. Notably, the gel used in these embodiments is subject to damage if excessive force is applied to exposed surfaces thereof. Likewise, excessive cyclical loads placed on the gel can damage the electrical components of the package, including the bond wires used to establish electrical connections between sensor elements. As the gel has significant mass, these pressure sensors also tend to be sensitive to accelerative forces, which can lead to inaccurate measurements.

Alternative pressure sensor systems and methods are desired.

SUMMARY

In one embodiment of the present disclosure a sensor for measuring pressure is provided. The sensor includes a substrate having a first housing defining a gas-filled interior cavity arranged thereon. An elastic sealing element is attached to a free end of the first housing and generally covers an open end of the interior cavity for sealing the interior cavity with respect to an external environment. A portion of the elastic sealing element is configured to be moveable in response to a pressure acting thereon. A semiconductor die is arranged on the substrate and defines a pressure sensing diaphragm exposed to the gas occupying the interior cavity.

In another embodiment of the present disclosure, a pressure sensor comprises a first housing defining a first cavity space formed therein. A semiconductor die is in communication with the first cavity space and is configured to convert a pressure acting thereon into a corresponding electrical signal. An elastic sealing element is arranged on the first housing and covers an open end of the first cavity space. A portion of the elastic sealing element is configured to be moveable in response to a pressure acting thereon. A mechanical stop is arranged between the moveable portion of the elastic sealing element and the semiconductor die.

In yet another embodiment of the present disclosure, a method of measuring a physiological signal such as a heart rate of a patient is provided. The method includes the step of placing an exposed side of an elastic pressure-sensitive sealing element of a heart rate sensor in contact with the patient. A pressure acting on the exposed side of the pressure-sensitive sealing element and transmitted through a gas-filled interior of a housing of the heart rate sensor is detected with a pressure-sensing semiconductor die exposed to the gas-filled interior of the housing.

DETAILED DESCRIPTION

Figure 1A:
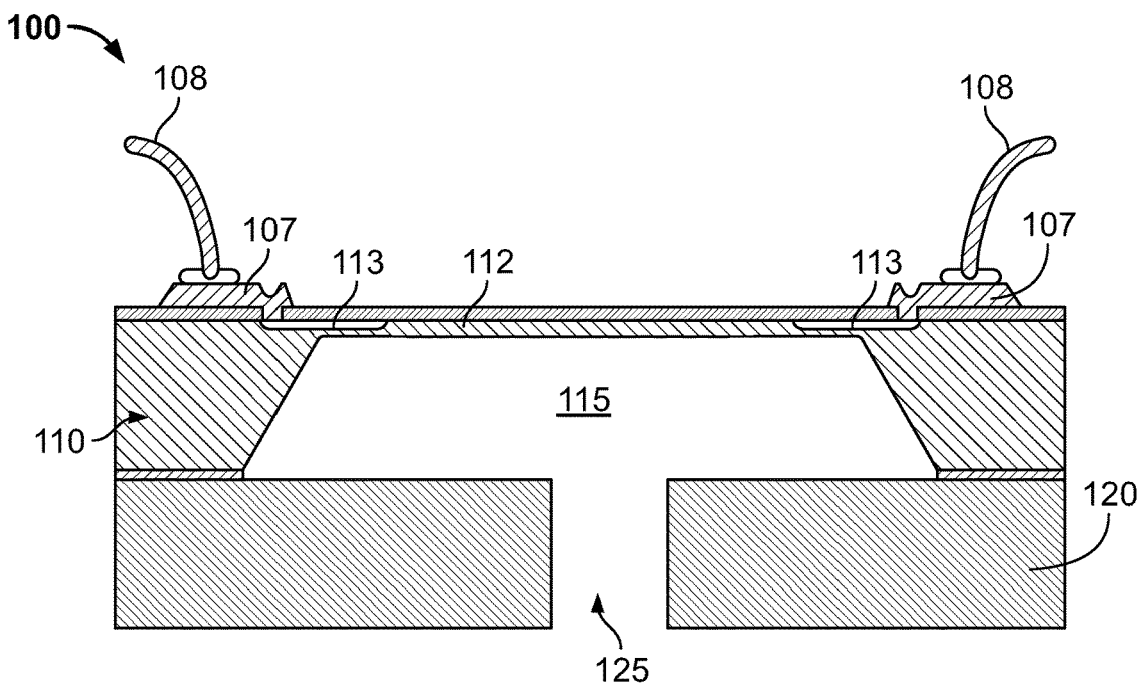
FIG. 1A is a cross-sectional view of a gauge or differential pressure sensor package according to the prior art.

It is to be understood that the figures and descriptions of the present invention have been simplified to illustrate elements that are relevant for a clear understanding of the present invention, while eliminating, for purposes of clarity, many other elements found in typical sensing systems, such as MEMS-based pressure sensors. However, because such elements are well known in the art, and because they do not facilitate a better understanding of the present invention, a discussion of such elements is not provided herein. The disclosure herein is directed to all such variations and modifications known to those skilled in the art.

In the following detailed description, reference is made to the accompanying drawings that show, by way of illustration, specific embodiments in which the invention may be practiced. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout several views.

Figure 1B:
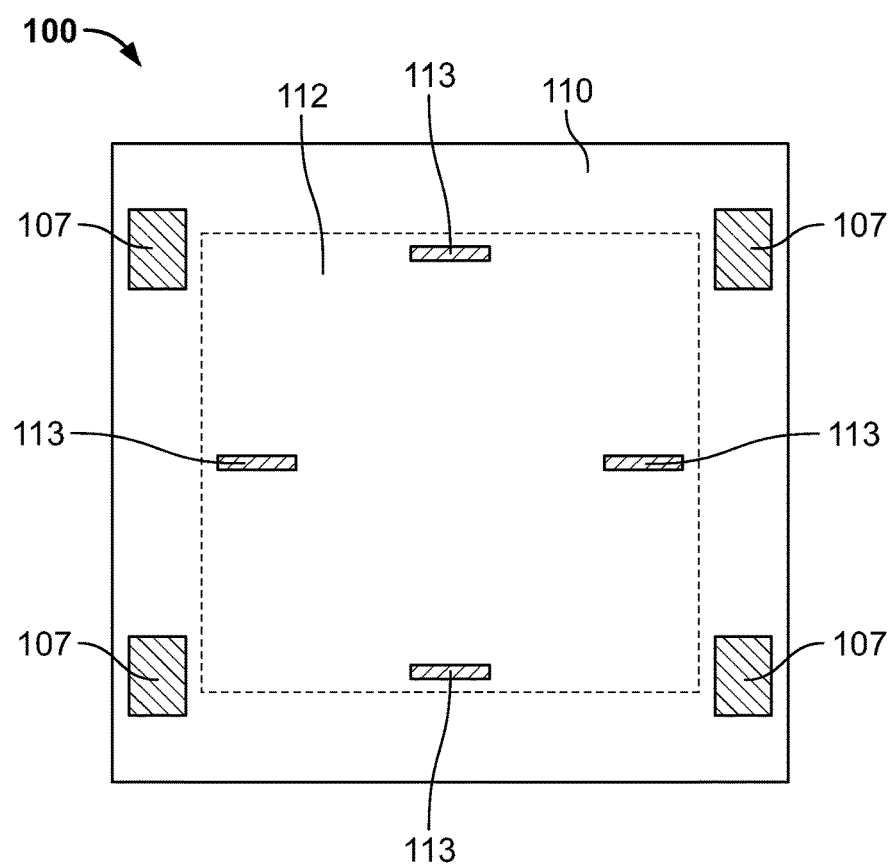
FIG. 1B is a simplified top view of the pressure sensor package of FIG. 1A.

FIGS. 1A and 1B illustrate a simplified MEMS pressure sensor package 100 of the prior art. Pressure sensor package 100 includes a sensing device or sensing die 110 formed from, for example, a semiconductor material such as a silicon wafer. As illustrated, die 110 has been selectively thinned to define a cavity 115 and a corresponding diaphragm 112. Die 110 may be thinned by any suitable means, for example, using anisotropic or dry etching as known in the art. One or more piezo-resistive elements 113, for example, are placed or formed on a surface of diaphragm 112. Each element 113 is configured to exhibit a resistance that is proportional to the strain placed on the thinned semiconductor material defining diaphragm 112. Thus, deflection of diaphragm 112 in response to a pressure acting thereon applies strain to elements 113.

Figure 2:
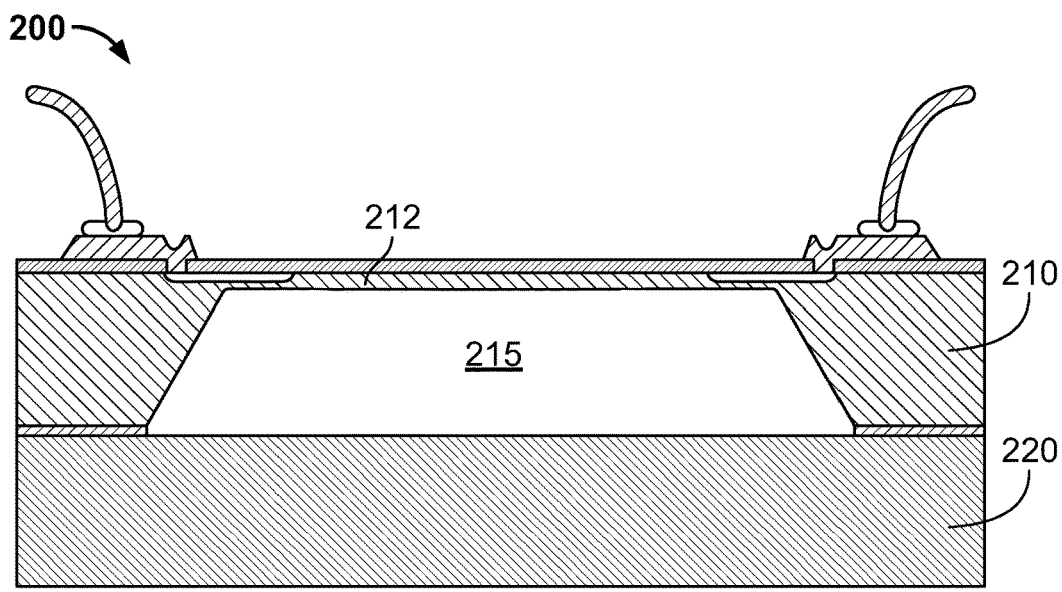
FIG. 2 is a cross-sectional view of an absolute pressure sensor package according to the prior art.

Pressure sensing die 110 may be mounted directly to a substrate (e.g. a ceramic or PCB substrate) via, for example, an adhesive material. In the illustrated embodiment, die 110 is mounted to a support structure or constraint 120 which is bonded or otherwise adhered to the substrate for isolating die 110 from interfering sources of strain, such as the thermal expansion of the substrate material. An opening or aperture 125 may be defined in constraint 120 for providing communication between a reference pressure source (e.g. atmospheric or other reference pressure) and an underside of a diaphragm 112 of die 110, by way of non-limiting example only. In this way pressure sensor package 100 may be configured as a gauge pressure sensor or a differential pressure sensor. It should be understood that other pressure sensor packages may be configured to perform absolute pressure measurements. As illustrated in FIG. 2, absolute pressure sensor package 200 comprises features similar to those of pressure sensor package 100 of FIGS. 1A and 1B, however, an aperture may not be formed in a mounting substrate and/or constraint 220. Rather, cavity 215 may be maintained in vacuum while a top side of diaphragm 212 of die 210 is exposed to a medium to be measured.

Referring again to FIGS. 1A and 1B, electrical connections between pressure sensing die 110 and electrical features such as bond pads, metalized conductors, or electrical components such as one or more ASICs, may be made via one or more bond wires 108 attached to bond pads 107 formed on die 110. These features may be mounted to or formed on a substrate of the sensor package, or arranged remotely therefrom. When a force is exerted on die 110, an electrical signal supplied through piezo-resistive elements 113 varies responsive to the deflection of diaphragm 112. Thus, a resulting output electrical signal is representative of the force applied to the surface of the pressure sensing die 110. An output electrical signal may be provided via bond wires 108 to other system circuitry, such as a control or calibration circuit for generating pressure data from the output electrical signal. This pressure data may be stored, by way of non-limiting example, in an electronic memory. Pressure data may also be provided to other processing components for purposes such as display, control signals, actuation, diagnostic purposes or other purposes.

Figure 3:
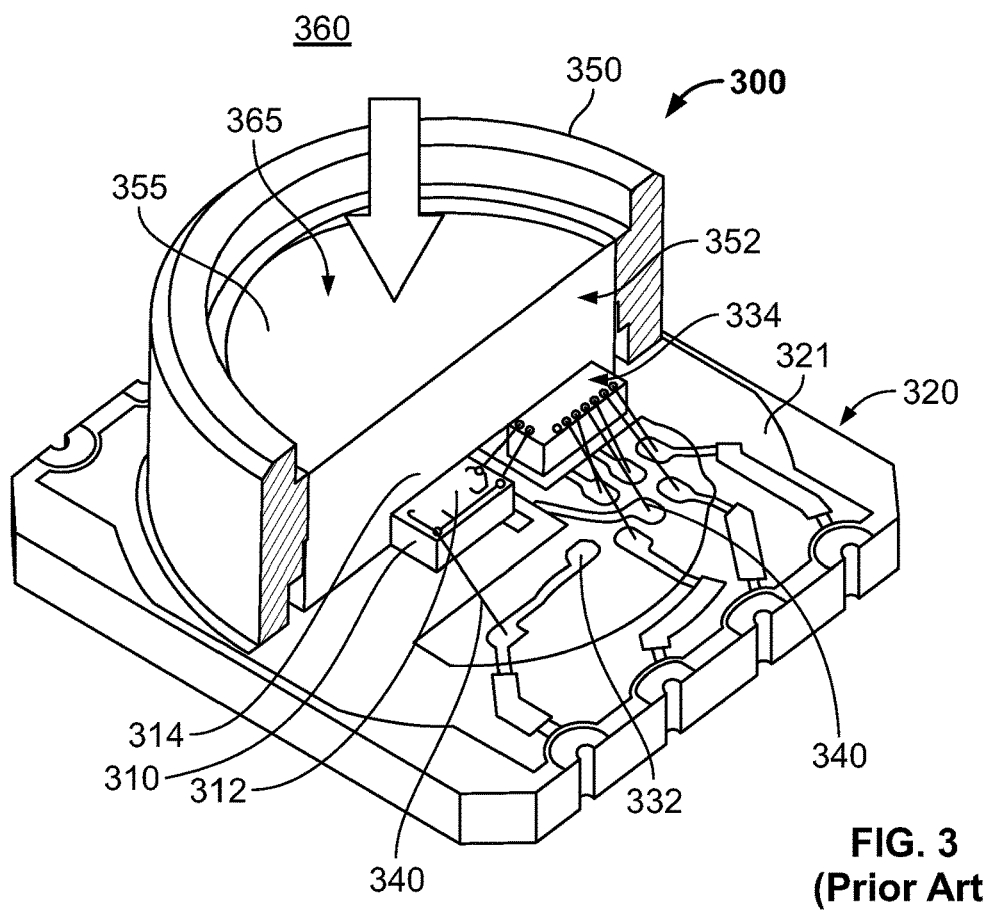
FIG. 3 is a partial cross-sectional view of a gel-filled pressure sensor package according to the prior art.

Referring generally to FIG. 3, a pressure sensor package 300 utilizing a gel-filled housing according to the prior art is shown. Pressure sensor package 300 includes a pressure sensing die 310, such as a semiconductor (e.g. silicon) die. As set forth above, die 310 may be selectively thinned to form a diaphragm 312 having, for example, piezo-resistive elements 314 arranged thereon for detecting diaphragm strain in response to pressure acting thereon. Die 310 is mounted to a substrate 320, such as a ceramic or PCB substrate. Substrate 320 may be selectively metalized on a first or top surface 321 thereof for forming electrically conductive features for establishing operational connections with die 310. By way of example, one or more conductive traces 332 may be formed on top surface 321. Bond wires 340 may also be provided for forming electrical connections between die 310 and conductive traces 332. Other electrical components, such as one or more ASICs 334, may also be arranged on substrate 320 for providing additional functionality to the package. This signal conditioning circuitry may provide for, for example, amplification, analog-to-digital conversion, offset compensation circuitry, and/or other suitable signal conditioning electronics.

Sensor package 300 further comprises a generally hollow cylindrical housing 350. Housing 350 is arranged on substrate 320 and generally over die 310, ASIC 334, portions of conductive traces 332 and bond wires 340, such that these features are arranged within an interior cavity 352 defined by housing 350. A force-transmitting or communicating gel or other elastomeric material 355 is used to fill interior cavity 352. In operation, force acting on a sensing end 365 of housing 350 in the indicated direction is communicated to diaphragm 312 of die 310 via gel 355. In addition to transmitting force, gel 355 functions to protect and/or isolate die 310, ASIC 334, conductive traces 332 and bond wires 340 from an external environment 360. In addition to causing inaccuracies under certain conditions (e.g. when the sensor is subject to accelerative forces), gel 355 is known to cause damage to bond wires 340 and/or other sensitive components within interior cavity 352 under certain conditions.

Figure 4A:
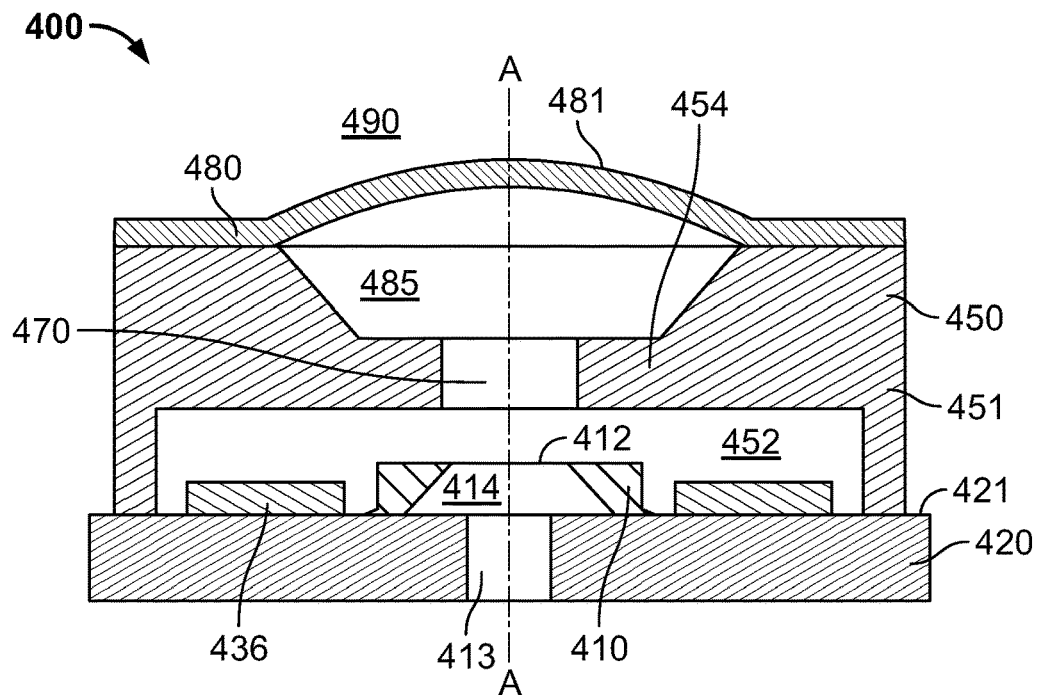
FIG. 4A is a cross-sectional view of a pressure sensor package according to an embodiment of the present disclosure.
Figure 4B:
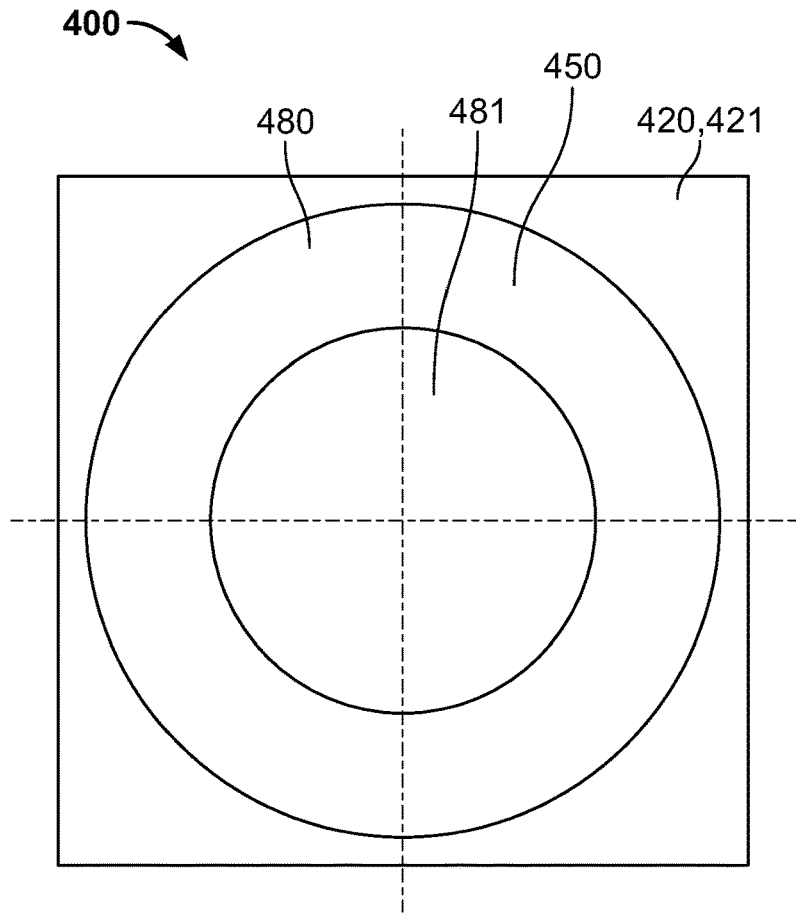
FIG. 4B is a top view of the pressure sensor package of FIG. 4A.
Figure 4C:
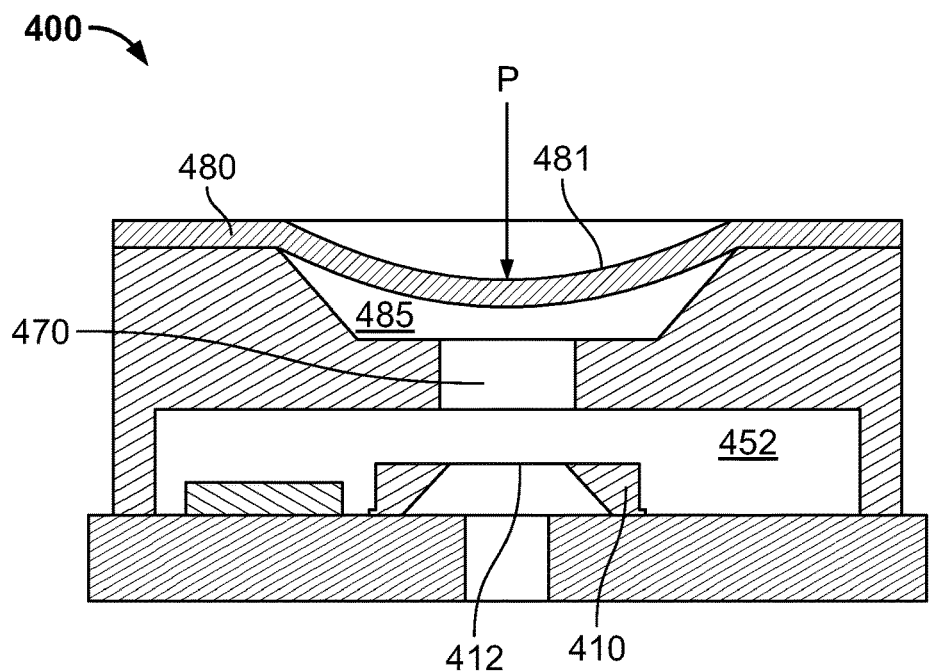
FIG. 4C is another cross-sectional view of the pressure sensor package of FIG. 4A.

FIGS. 4A, 4B and 4C illustrate a simplified pressure sensor package 400 according to an embodiment of the present disclosure. In the exemplary embodiment, pressure sensor package 400 includes a pressure sensing die 410 defining a diaphragm 412. Die 410 comprises, by way of example only, a plurality of piezo-resistive elements configured to detect diaphragm strain. Die 410 is mounted on a first or top surface 421 of a substrate 420 (e.g. a ceramic or PCB substrate) forming a hermetic seal therewith around its perimeter. In some embodiments, pressure sensor package 400 may be embodied as an absolute pressure sensor package, whereby aperture 413 is not present, and a cavity 414 defined between die 410 and top surface 421 of substrate 420 is held in vacuum. In other embodiments, pressure senor package may be embodied as a gauge or differential pressure sensor, wherein die 410 is mounted over optional aperture 413 formed through substrate 420 such that pressure sensing diaphragm 412 is also exposed to reference pressure source via aperture 413. Optionally, one or more components, such as an ASIC 436 are also arranged on top surface 421 of substrate 420. Electrical connections between ASIC 436 and die 410 (as well as other components) may be made via bond wires.

In one embodiment, ASIC 436 is configured (i.e. programmed) to, in response to positioning the sensor onto a body surface and receiving a pressure or force acting on pressure sensing die 410, generate a value indicative of a heart rate of a patient. This value is indicative of the frequency of detected pressure or detected pressure peaks acting on pressure sensing die 410 and thus, corresponds to the frequency of contractions of a heart of the patient or beat to beat intervals (e.g. beats per minute or BPM). While an ASIC is illustrated, it is contemplated that signal conditioning circuitry may be provided in any suitable form, such as by one or more microprocessors or microcontrollers, as desired for performing the desired functions.

Sensor package 400 further comprises a housing or housing member 450 (e.g. a metallic or polymer housing) arranged on top surface 421 of substrate 420. In one embodiment, housing 450 may comprise a generally cylindrical outer profile. Housing 450 includes a body portion having a peripheral wall 451 defining a first cavity space or recess 452 at a first end thereof. As shown, first cavity space 452 is defined generally between a protrusion or wall portion 454 of peripheral wall 451 that extends radially-inward with respect to a central axis A of sensor package 400 and top surface 421 of substrate 420. Peripheral wall 451 of housing 450 further defines a second cavity space 485 at a second end of housing 450. First cavity space 452 and second cavity space 485 are at least partially separated from one another by wall portion 454. Wall portion 454 of peripheral wall 451 further defines an aperture 470. Aperture 470 is configured (i.e. sized and located) to provide fluid (e.g. air) communication between first cavity space 452 and second cavity space 485, and thus between second cavity space 485 and diaphragm 412 of die 410.

An elastic sealing element or cap 480 is provided and configured to attach to the open second end of housing 450 and generally over second cavity space 485. Sealing element 480 is configured to isolate second cavity space 485 from an external environment 490 such that once fitted, first and second cavity spaces 452,485, as well as aperture 470, are filled with a fixed or closed volume of fluid (e.g. gas), such as air under atmospheric pressure. Sealing element 480 may comprise a moveable dome-shaped or arcuate portion 481 of which protrudes in a direction away from second cavity space 485 in an unbiased state (wherein no external forces are acting thereon sufficient to deform the element). Arcuate portion 481 is configured so that its outer surface is to be placed into contact with, for example, the skin of a patient for enable sensing operations, such as heart rate monitoring.

Referring generally to FIG. 4C, in operation, a force acting on sealing element 480 in the indicated direction P is operative to flex a portion of sealing element 480 (e.g. arcuate portion 481) in a like direction, pressurizing the fixed volume of gas maintained within housing 450 (i.e. within first and second cavity spaces 452,485 and aperture 470). In this way, sealing element 480 acts as a diaphragm for transmitting pressure acting thereon to diaphragm 412 of die 410. Accordingly, the elasticity and/or stiffness of sealing element 480 should be selected such that a suitable sensitivity is achieved for a desired application. Moreover, as set forth above, wall portion 454 of peripheral wall 451 extends generally from an outer or peripheral portion of housing 450, radially inward toward a central axis (axis A, FIG. 4A) of sensor package 400. Accordingly, at least some of wall portion 454 is arranged generally beneath sealing element 480, and more specifically movable arcuate portion 481 thereof, in an axial direction. According, wall portion 454 is configured as a mechanical stop, limiting excessive downward motion (i.e. motion in the direction of pressure P) of sealing element 480, and thus protecting, for example, sensing die 410 from damage therefrom.

Figure 5A:
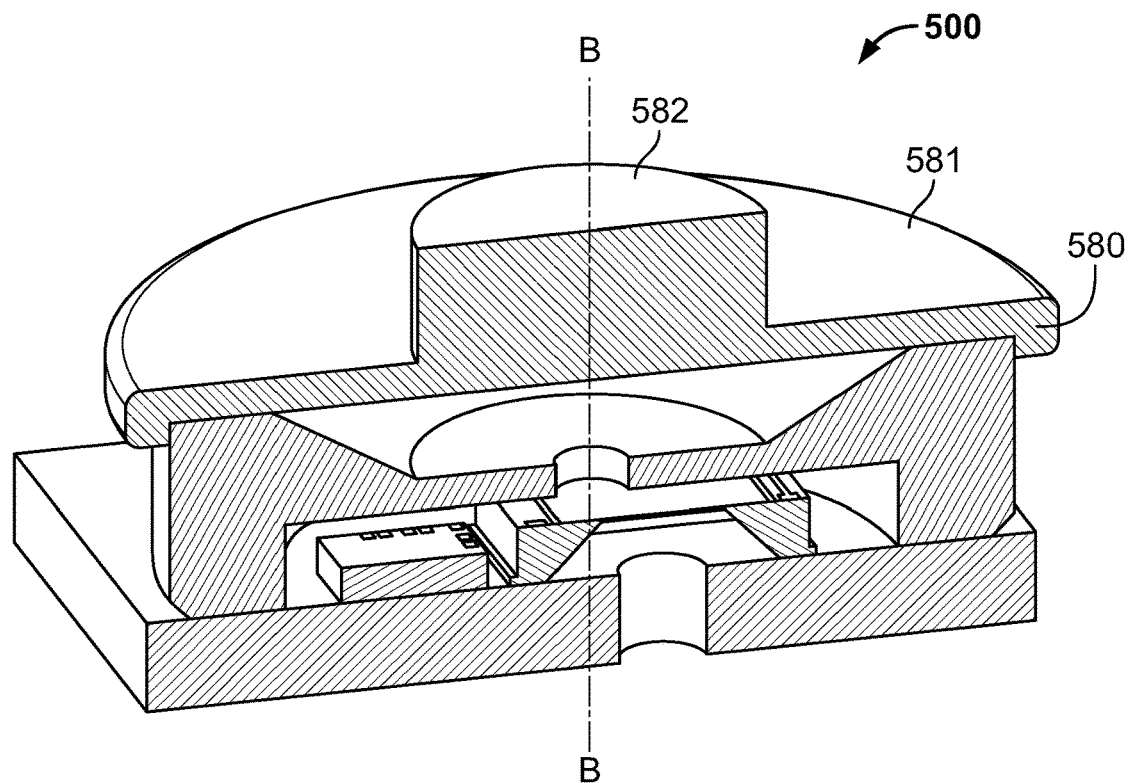
FIG. 5A is a cross-sectional view of a pressure sensor package according to another embodiment of the present disclosure.
Figure 5B:
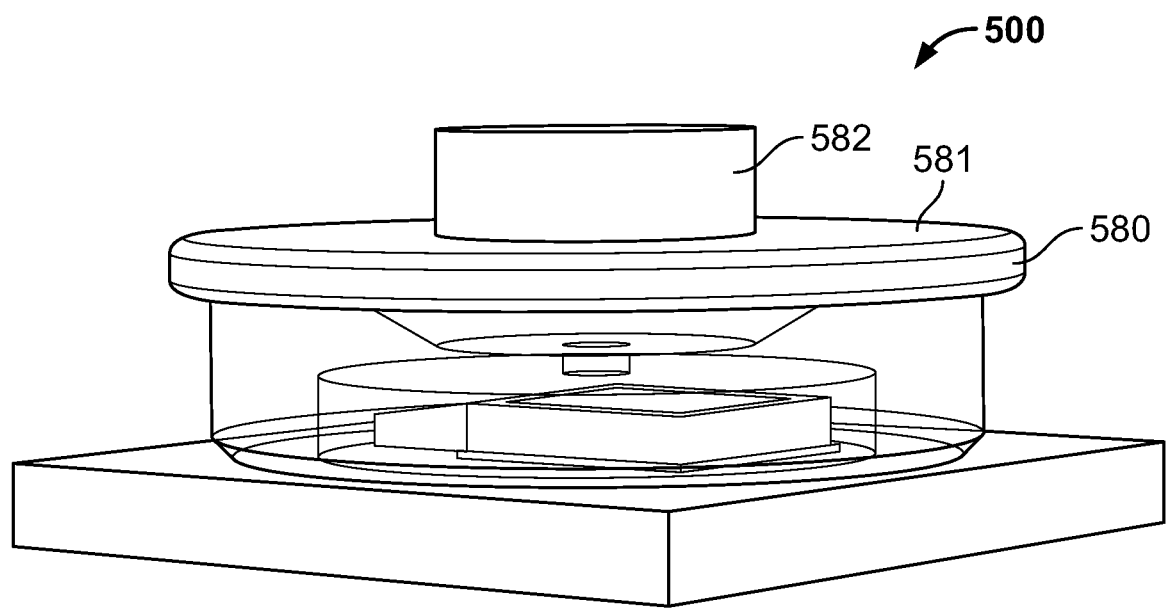
FIG. 5B is perspective view of the pressure sensor package of FIG. 5A.

As shown in FIGS. 5A and 5B, in an alternate embodiment of the present disclosure, a sealing element 580 of a sensor package 500 having features similar to those set forth above with respect to FIGS. 4A-4C may comprise a generally flat or planar profile 581 and may have a protrusion 582 (e.g. a cylindrical protrusion) extending generally perpendicularly therefrom for engaging with a measurement surface (e.g. a patient's skin). Protrusion 582 may be located generally coaxially with a central axis B of pressure sensor package 500.

Figure 6A:
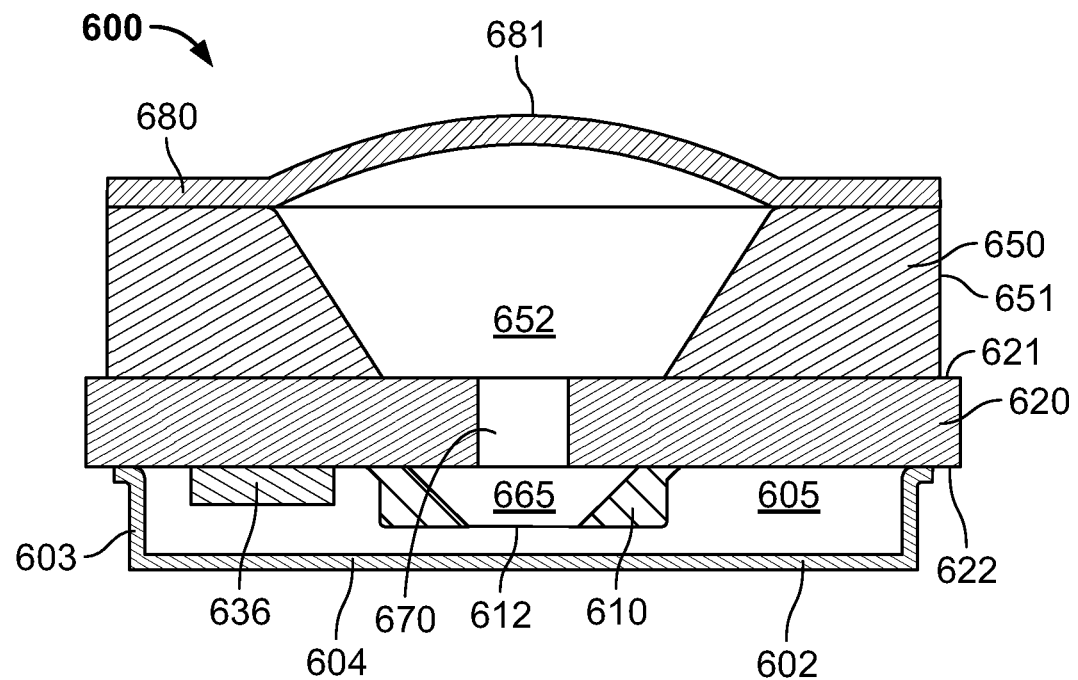
FIG. 6A is a cross-sectional view of a pressure sensor package according to another embodiment of the present disclosure.
Figure 6B:
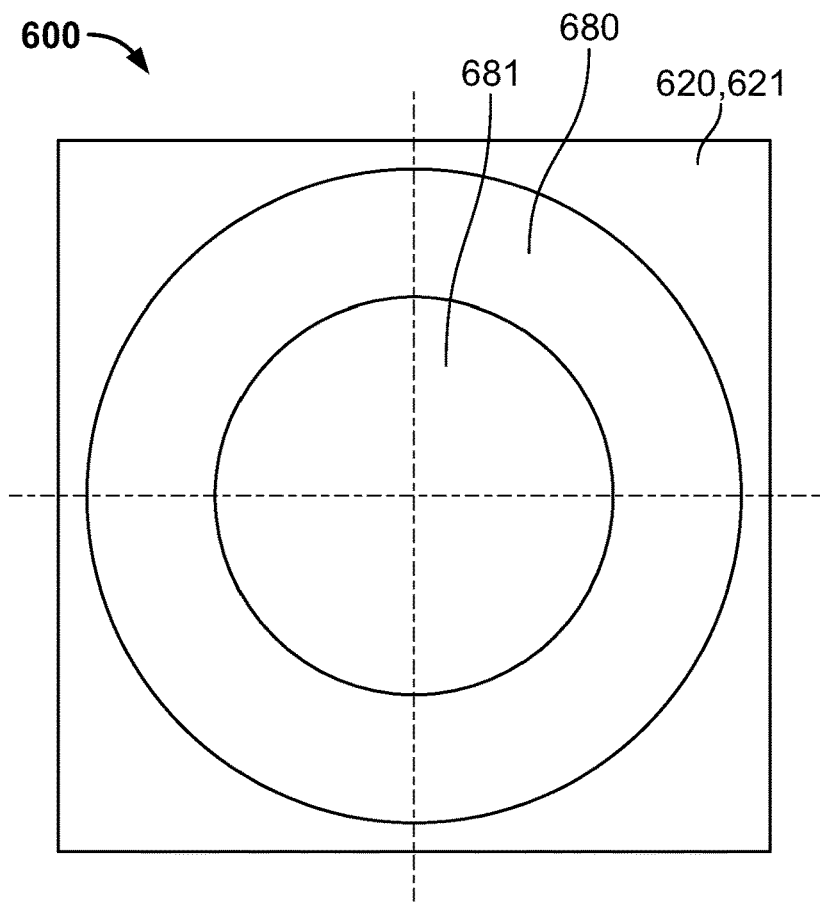
FIG. 6B is a top view of the pressure sensor package of FIG. 6A.
Figure 6C:
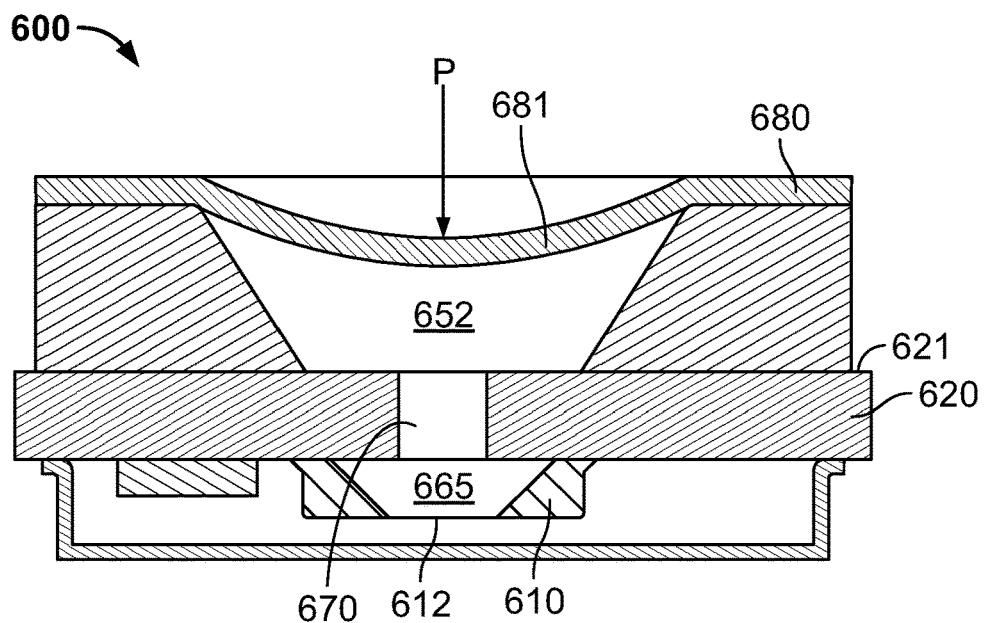
FIG. 6C is another cross-sectional view of the pressure sensor package of FIG. 6A.

FIGS. 6A-6C illustrate another pressure sensor assembly or package 600 according to an embodiment of the present disclosure. Package 600 includes a sensing die 610 defining a diaphragm 612. Die 610 may comprise, by way of example, only, a plurality of piezo-resistive elements or other elements configured to detect diaphragm strain or other characteristics indicative of pressure acting thereon. Die 610 is mounted (e.g. via an adhesive) to a bottom surface 622 of a substrate 620 (e.g. a ceramic or PCB substrate), forming a hermetic seal therewith around its perimeter. One or more components, such as an ASIC 636 may also be attached to bottom surface 622 of substrate 620. Electrical connections between ASIC 636 and die 610 (as well as other components) may be made via bond wires (not shown), as is understood in the art.

Sensor package 600 further comprises a first housing or housing member 602 (e.g. a metallic or polymer housing) arranged over die 610 and ASIC 636 and attached to (e.g. via an adhesive) bottom surface 622 of substrate 620. In one embodiment, first housing 602 may be generally cylindrical in profile and includes a peripheral or annular wall 603 and an end wall 604 defining a first cavity space or recess 605. First housing 602 is configured to isolate first cavity space 605, including die 610 and ASIC 636, from an external environment 690. As illustrated, pressure sensor package 600 may be embodied as an absolute pressure sensor package, wherein first cavity space 605 is held in vacuum. In other embodiments, the pressure senor package may be embodied as a gauge or differential pressure sensor, wherein an aperture may be formed through first housing 602 such that pressure sensing diaphragm 612 is exposed to a reference pressure.

Sensor package 600 further comprises a second housing or housing member 650 (e.g. a metallic or polymer housing) arranged on a top surface 621 of substrate 620, generally opposite bottom surface 622. In one embodiment, second housing 650 may be generally hollow, including a peripheral or annular wall 651 defining a second cavity space or recess 652 formed therethrough. Substrate 620 further comprises an aperture 670 formed therethrough. Aperture 670 is configured (i.e. sized and located) to provide communication between first cavity space 605 and a third cavity space 665 defined between diaphragm 612 of die 610 and bottom side 622 of substrate 620.

An elastic sealing element or cap 680 is provided and configured to attach to housing 650 over an open end of second cavity space 652. Sealing element 680 is configured to isolate second cavity space 652 from an external environment 690 such that once attached, the second and third cavity spaces 652,665 as well as aperture 670, are occupied by a fixed or closed volume of gas, such as air. As set forth above, sealing element 680 may comprise a moveable arcuate portion 681 which protrudes in a direction away from second cavity space 652 in an unbiased state. Arcuate portion 681 is configured to be placed into contact with, for example, the skin of a patient for enabling heart rate sensing. As set forth above with respect to FIGS. 5A and 5B, alternative sealing elements may be utilized in the embodiment of FIGS. 6A-6C without departing from the scope of the present disclosure.

As illustrated in FIG. 6C, in operation, a force acting on sealing element 680 in the indicated direction P is operative to flex or displace arcuate portion 681 of sealing element 680 in a like direction. In this way, sealing element 680 acts to transmit pressure acting thereon through second and third cavity spaces 652,665 via aperture 670, and thus onto diaphragm 612 of die 610 where it may be detected. It should be understood that as at least a portion of substrate 620 is arranged generally beneath moveable arcuate portion 681 of sealing element 680 with respect to the direction of force P. In this way, top surface 621 of substrate 620 is configured as a mechanical stop for limiting excessive travel (i.e. motion in the direction of pressure P) of arcuate portion 681 of sealing element 680 for protecting, for example, sensing die 610 from damage therefrom.

While embodiments of the present disclosure have been described as utilizing, for example, piezo-resistive elements to detect strain of a pressure-sensing diaphragm, it should be understood that any suitable type of pressure-sensing technology may be implemented without departing from the scope of the present disclosure. For example, pressure sensors disclosed herein may implement capacitive, electromagnetic, piezoelectric, optical or thermal pressure-sensing techniques, as will be understood by one of ordinary skill in the art.

While the foregoing invention has been described with reference to the above-described embodiment, various modifications and changes can be made without departing from the spirit of the invention. Accordingly, all such modifications and changes are considered to be within the scope of the appended claims. Accordingly, the specification and the drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations of variations of various embodiments. Combinations of the above embodiments, and other embodiments not specifically described herein, will be apparent to those of skill in the art upon reviewing the above description.

What is claimed is:

1. A pressure sensor comprising:
a substrate;
a first housing defining a gas-filled interior cavity arranged on the substrate;
an elastic sealing element attached to a first end of the first housing and generally covering an open end of the interior cavity for sealing the interior cavity with respect to an external environment, wherein a portion of the elastic sealing element is configured to be moveable in response to a pressure acting thereon; and
a semiconductor die arranged on the substrate and defining a pressure sensing diaphragm exposed to the gas occupying the interior cavity.

2. The pressure sensor of claim 1, wherein the interior cavity includes:
a first cavity space defined in the first end of the first housing;
a second cavity space defined in a second end of the first housing; and
an aperture defined in the first housing for providing fluid communication between the first cavity space and the second cavity space,
wherein the semiconductor die is arranged within the second cavity space.

3. The pressure sensor of claim 2, wherein at least a portion of the first housing is arranged between the moveable portion of the elastic sealing element and the second cavity space.

4. The pressure sensor of claim 3, wherein the first and second cavity spaces and the aperture are occupied by an enclosed volume of gas.

5. The pressure sensor of claim 1, wherein the elastic sealing element is configured to transmit a force acting on a surface thereof to the pressure sensing diaphragm.

6. The pressure sensor of claim 1, further comprising an application specific integrated circuit (ASIC) arranged on the substrate, wherein the ASIC is configured to generate an output electrical signal indicative of a detected pressure fluctuation by the pressure sensing diaphragm of the semiconductor die corresponding to a heart beat rate.

7. The pressure sensor of claim 1, wherein the elastic sealing element comprises a protrusion extending from an exposed side thereof in a direction away from the interior cavity.

8. The pressure sensor of claim 1, wherein the first housing is arranged on a first surface of the substrate, and wherein the pressure sensor further comprises a second housing arranged on a second surface of the substrate, opposite the first surface, the second housing defining a second interior cavity.

9. The pressure sensor of claim 8, wherein the semiconductor die is arranged on the second surface of the substrate and within the second interior cavity of the second housing, and wherein the pressure sensing diaphragm of the semiconductor die is in fluid communication with the interior cavity via an aperture formed through the substrate.

10. The pressure sensor of claim 9, wherein at least a portion of the substrate is arranged between the moveable portion of the elastic sealing element and the pressure sensing diaphragm of the semiconductor die.

11. The pressure sensor of claim 9, wherein the interior cavity and the aperture are occupied by an enclosed volume of gas.

12. The pressure sensor of claim 9, further comprising an application specific integrated circuit (ASIC) arranged on the second surface of the substrate and within the second interior cavity defined by the second housing.

13. The pressure sensor of claim 1, wherein the first housing comprises one of a polymer housing and a metallic housing.

14. The pressure sensor of claim 1, wherein the elastic sealing element comprises an arcuate portion that protrudes in a direction away from interior cavity in an unbiased state.

* * * * *